United States Patent [19]

Chazerain et al.

[11] 4,302,458
[45] Nov. 24, 1981

[54] PHTHALIDYL-ISOQUINOLINE DERIVATIVES

[75] Inventors: Jacques A. Chazerain, Ville d'Avray; Hubert Y. Cotereau, Neuilly-sur-Seine; Pierre H. Lallouette, Sannois; Hugues A. Legger, Courbevoie; Pierre A. C. Lepape, Paris, all of France

[73] Assignees: Laborec Laboratoire de Recherches Biologiques, Asnieres; Calaire Chimie, S.A., Calais, both of France

[21] Appl. No.: 87,799

[22] Filed: Oct. 24, 1979

[51] Int. Cl.³ .................. C07D 405/04; A61K 31/47
[52] U.S. Cl. .................................. 424/258; 544/139; 544/144; 260/343.3 R
[58] Field of Search ................. 546/139, 144; 424/258

[56] References Cited

U.S. PATENT DOCUMENTS 3,277,085 10/1966 Aebi et al. .................. 546/139
3,796,712 3/1974 Leimgruber et al. ........... 546/139

FOREIGN PATENT DOCUMENTS 1295309 5/1962 France .
2424271 11/1979 France .
873935 8/1961 United Kingdom .

OTHER PUBLICATIONS

Merck Index, 1976, p. 1252, Abstract No. 9428.
Merck Index, 1976, p. 872, Abstract No. 6528.
Kosmicki, et al., "J. Pharmacol" (Paris), vol. 5(3), 1974, pp. 331-342.
Taylor, J. Chim. Soc., 1951, pp. 1150-1157.
Brossi, "Helv. Chem. Acta", vol. 47(7), 1964, pp. 2089-2097.
Schenker, et al., "Helvetica Chimica Acta", vol. 47, No. 232, 1964, pp. 2089-2097.

Primary Examiner—Donald G. Daus
Assistant Examiner—James H. Turnipseed
Attorney, Agent, or Firm—Wegner & Bretschneider

[57] ABSTRACT

The phthalidyl-isoquinoline derivatives have the formula:

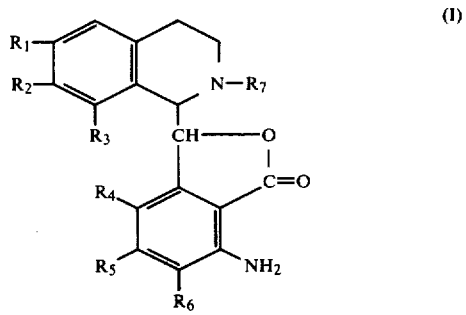

in which $R_1$, $R_2$, $R_4$, $R_5$ and $R_6$ each denotes a lower alkoxy group, $R_3$ denotes a hydrogen atom or a lower alkoxy group and $R_7$ denotes a lower alkyl group and also include their diastereoisomers and their addition salts with pharmaceutically acceptable acids.

These compounds have antiallergic activities and may be used to treat allergic symptoms in human beings and other animals.

9 Claims, No Drawings

PHTHALIDYL-ISOQUINOLINE DERIVATIVES

The present invention relates to derivatives of phthalidyl-isoquinolines, their preparation, and their use as medicaments, in particular for treating allergy conditions.

Noscapine has been known for a long time, which is an alkaloid used on account of its antitussive properties. A derivative structurally similar to this latter compound, namely tritoqualine (see French Pat. No. 1 295 309) has been noted for its anti-allergy properties (HAHN et al, Arz. Forsch. 20, 1490 (1970)).

It has now been found that new compounds of this type have a similar but even more useful activity, and may thus be used in therapeutics.

The compounds of the invention have the formula $$(I)$$

in which $R_1$, $R_2$, $R_4$, $R_5$ and $R_6$ each denotes a lower alkoxy group, $R_3$ denotes a hydrogen atom or a lower alkoxy group, and $R_7$ denotes a lower alkyl group, as well as their diastereoisomers and their addition salts with pharmaceutically acceptable acids.

By the term lower alkyl and alkoxy groups are meant groups having at most 4 carbon atoms, in particular the methyl and methoxy or ethoxy radicals respectively.

The compounds of the formula (I) may be prepared by catalytic or chemical reduction of the corresponding nitro derivative of formula $$(II)$$

in which the various symbols have the same meaning as in formula (I).

The nitro derivatives (II) may be prepared by condensing an ammonium salt of a substituted dihydro-isoquinoline (III) with a trialkoxy-phthalide (IV) according to the following reaction scheme:

$$(III), R_7X \qquad (IV)$$

In these formulae the various symbols $R_1$ to $R_7$ have the same meaning as in formula (I), and $X^-$ is an anion such as $OH^-$, $Cl^-$, $Br^-$, $I^-$ or $CH_3SO_4^-$. The reaction is carried out in a basic medium and preferably in a lower alcohol at a temperature below its boiling point.

The derivatives of formula (IV) are known according to French Pat. No. 1 295 309.

The ammonium salts of the substituted dihydroxy-isoquinolines (III, $R_7X$) are known in part, and may be prepared in a conventional manner by addition of a compound $R_7X$ to the substituted dihydroxy-isoquinoline (III). The latter may be prepared by formylating a substituted phenylethylamine, followed by cyclisation, according to the reaction scheme $$\xrightarrow{HCOOH}$$

$$\xrightarrow{POCl_3} III$$

In these formulae the symbols $R_1$, $R_2$ and $R_3$ have the same meaning as above. The formylation reaction is carried out in a conventional manner by means of formic acid and acetic anhydride at a temperature ranging from 25° to 80° C. The cyclisation may be carried out with phosphorus oxychloride at a temperature ranging from 50° to 100° C.

The following examples illustrate the invention.

EXAMPLE A 2-methyl-6,7,8-trimethoxy-3,4-dihydroisoquinolinium iodide (intermediate product III, $R_7X$; $R_1$, $R_2$, $R_3=OCH_3$, $R_7=CH_3$ and $X=I$)

(a) 2-formyl-3,4,5-trimethoxy-phenylethylamine 1.422 kg of 3,4,5-trimethoxy-phenylethylamine is slowly added to a mixture of 2.185 kg of 98% formic acid and 1.728 kg of acetic anhydride, while maintaining the temperature at about 50°. The reaction bath is maintained at this temperature for about 3 hours and the formic acid and acetic acid mixture and the excess anhydride is distilled. The formylated derivative thus obtained (1.734 kg) is used unpurified.

(b) 6,7,8trimethoxy-3,4-dihydroisoquinoline

The formylated derivative obtained above and 3 liters of toluene are added to a reactor at a temperature of about 70°, 1.385 kg of phosphorus oxychloride is then added, and the reaction mixture is maintained at this temperature for about 2 hours. The reaction mixture is then cooled to below 50° and poured into 5.1 liters of water and 1.8 kg of crushed ice. The acid aqueous phase is separated, made alkaline with a solution of 40% sodium hydroxide, and is then extracted with toluene. The toluene is removed in vacuo and the 6,7,8-trimethoxy-3,4-dihydro-isoquinoline is used in the unpurified state.

(c)

2-methyl-6,7,8-trimethoxy-3,4-dihydro-isoquinolinium iodide 1.9 kg of 6,7,8-trimethoxy-3,4-dihydro-isoquinoline and 7 liters of acetone are added to a reactor, followed by 2.1 kg of methyl iodide, the temperature being kept below 50°. The reaction mixture is then heated under reflux for 30 minutes, a further 200 g of methyl iodide is added, and the mixture is refluxed for about a further hour.

The reaction mixture is cooled to below 20°, and the iodomethylate is dried under suction and washed with a small amount of acetone. 2.300 kg are obtained.

EXAMPLE 1

2-methyl-6,7,8-trimethoxy-1[4,5,6-triethoxy-7-amino-3-phthalidyl]-1,2,3,4-tetrahydro-isoquinoline (Code No. 458 L)

(a)

2-methyl-6,7,8-trimethoxy-1[4,5,6-triethoxy-7-nitro-3-phthalidyl]-1,2,3,4-tetrahydro-isoquinoline 235 g (0.647 mole) of 2-methyl-6,7,8-trimethoxy-3,4-dihydro-isoquinolinium iodide (described in J. Chem. Soc. 1951, 1150), 201.4 g of 4,5,6-triethoxy-7-nitrophthalide and 107 g of potassium carbonate are added to 1.240 liters of methanol. After stirring for 24 hours at a temperature below the boiling point of the solvent, 730 ml of water is added and the reaction solution is allowed to crystallise. The crystals are collected by filtration, washed with water and dried, providing 270 g of $C_{27}H_{34}O_{10}N_2$.

M.p. 116–140°.

(b)

2-methyl-6,7,8-trimethoxy-1-[4,5,6-triethoxy-7-amino-3-phthalidyl]-1,2,3,4-tetrahydro-isoquinoline 270 g of the nitro derivative (a) is added to 1.570 liters of ethanol and 21 g of Raney nickel in an autoclave. Hydrogen is added under a pressure of 10 atmospheres and the reactants are heated at a temperature of 65° while stirring. After 1 hour 45 minutes the theoretical volume of hydrogen has been absorbed. The solution is cooled and filtered. The ethanol is distilled in vacuo, the residue is dissolved in 0.6 l of methanol, 60 g of potassium hydroxide tablets are added, and the mixture is heated under reflux for 1 hour while stirring. The mixture is cooled and allowed to crystallise. 194.5 g (yield = 76%) of 2-methyl-6,7,8-trimethoxy-1-(4,5,6-triethoxy-7-amino-3-phthalidyl)-1,2,3,4-tetrahydro-isoquinoline is obtained in the form of white crystals having a melting point of 144° and exhibiting only a single spot when analysed by thin layer chromatography.

EXAMPLE 2

2-methyl-6,7-dimethoxy-1[4,5,6triethoxy-7-amino-3-phthalidyl]-1,2,3,4-tetrahydro-isoquinoline (a)

2-methyl-6,7-dimethoxy-1[4,5,6-triethoxy-7-nitro-3-phthalidyl]-1,2,3,4-tetrahydro-isoquinoline 200 g (0.6 mole) of 2-methyl-6,7-dimethoxy-3,4-dihydro-isoquinolinium iodide (prepared in the same manner as the compound of Example A) 186 g of 4,5,6-triethoxy-7-nitrophthalide and 100 g of potassium carbonate are added to 1.5 l of methanol while stirring. The reaction mixture is stirred for 24 hours at a temperature below the boiling point of the solvent, and is then allowed to cool; 900 ml of water is added and the reaction solution is allowed to crystallise. The solution is filtered, rinsed with methanol, and then with water.

On drying, 247 g of cream coloured crystals having the formula $C_{26}H_{32}O_9N_2$ are obtained.

(b)

2-methyl-6,7-dimethoxy-1[4,5,6-triethoxy-7-amino-3-phthalidyl]-1,2,3,4-tetrahydro-isoquinoline A Zn-Cu "couple" is first of all prepared:

350 g of zinc powder is washed by shaking in 500 ml of a 1% sodium hydroxide solution; the solution is decanted off and the solid material is then washed twice with water, the water being decanted off after each wash. 700 ml of a solution prepared by dissolving 17 g of cupric sulphate and 7 ml of concentrated sulphuric acid in 700 ml of water is then added to the washed powder. The mixture is shaken for 15 minutes and the supernatant solution is decanted.

Next, 500 ml of water is added to the Zn-Cu couple thus prepared, followed by the gradual addition, all the time while stirring, of the solution of 167 g of the nitro compound obtained in the previous stage (a) dissolved in 1 liter of acetic acid. Stirring is continued for 48 hours at a temperature of 20–25°. The couple is separated by filtration and the filtrate is partially concentrated in vacuo and 2.5 liters of water are added; the resultant solution is extracted 3 times with chloroform.

The chloroform extracts are combined, washed with a solution of sodium bicarbonate, and then with water. The extracts are dried by shaking with anhydrous sodium sulphate, and are then concentrated in vacuo.

The residue is dissolved in 500 ml of methanol, 50 g of potassium hydroxide tablets are added, and the reaction mixture is heated under reflux for 1 hour while stirring. The mixture is then cooled and allowed to crystallise. 115 g of 2-methyl-6,7-dimethoxy-1-[4,5,6-triethoxy-7-amino-3-phthalidyl]-1,2,3,4-tetrahydro-isoquinoline is isolated in the form of white crystals having a melting point of 143° C.

The compounds of the invention have been tried out in various pharmacological tests.

It has been found that the compounds of the invention are well tolerated by animals at dosages envisaged for their therapeutic application.

The toxicity was determined in the conventional manner. The LD 50 of the compound 458 L in mice by the oral route is about 6 g/kg, and chronic toxicity tests in mice showed that this product is well tolerated.

It has been found that the compound 458 L has interesting properties, in particular that of inhibiting in vivo the action of the enzyme histidine decarboxylase, thereby blocking the endogenous formation of histamine, whose pathological action in animals and humans is well known.

The activity of the compound 458 L was compared with that of tritoqualine, which is, to the Applicants' knowledge, the only product used therapeutically for this objective. The technique for measuring the histadine decarboxylase activity of guinea-pig kidneys has been described by B. Kosmicki et al (J. Pharmacol. Paris 1974-5-3-331-342). The guinea-pigs were sacrificed five hours after administering the substances under investigation. The percentage reduction in the activity of the renal enzyme of the treated animals was determined with respect to control animals. The results obtained are given in the following table:

| Dosage of product expressed in mg/kg | Activity expressed in % inhibition of the enzyme | |
|---|---|---|
| | 458 L | Tritoqualine |
| 10 | 14 | 10 |
| 20 | 21 | 20 |
| 40 | 31 | 20 |
| 60 | 41 | 22 |

It is thus found that the inhibitory activity may be as high as twice that of the reference product.

By virtue of their properties, the compounds of the invention and in particular 458 L may be used in the prevention and treatment of allergy conditions in animals and humans (pollinoses, urticaria, eczema, migraine, pruritus, etc.).

The compounds of the invention can be administered orally or rectally in a daily dosage of 20 to 500 mg. They may be made available for example in the form of tablets, pills or suppositories.

They may also be administered by inhalation in the form of aerosols of micronised powder, possibly diluted in an inert excipient (for example mannitol).

| Examples of formulations: | |
|---|---|
| Tablets | |
| Compound 458 L | 50 mg |
| Starch | 50 mg |
| Lactose | 100 mg |
| Talc | 10 mg |
| Magnesium stearate | as sufficient |
| Aerosol or spray | |
| Compound 458 L | 50 mg |

| -continued | |
|---|---|
| Examples of formulations: | |
| Mannitol | 150 mg |
| for one disposable capsule for aerosols. | |

We claim:
1. A compound of the formula

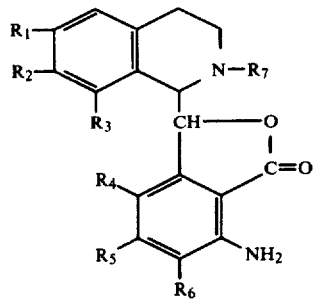

wherein
each of $R_1$, $R_2$, $R_4$, $R_5$ and $R_6$ is lower alkoxy;
$R_3$ is hydrogen or lower alkoxy; and
$R_7$ is lower alkyl
or a diasterioisomer thereof or a pharmaceutically acceptable acid addition salt thereof.

2. 2-methyl-6,7-dimethoxy-1-[4,5,6-triethoxy-7-amino-3-phthalidyl]-1,2,3,4-tetrahydro-isoquinoline.

3. A compound of claim 1, wherein $R_1$, $R_2$, $R_3$, $R_4$, $R_5$ and $R_6$ are each independently methoxy or ethoxy.

4. A compound of claim 1, wherein $R_7$ is methyl.

5. 2-methyl-6,7,8-trimethoxy-1-[4,5,6-triethoxy-7-amino-3-phthalidyl]-1,2,3,4-tetrahydro-isoquinoline.

6. A pharmaceutical composition for inhibiting an allergic condition in a patient which comprises a compound of claim, 2, 1, 3 or 4 and a physiologically acceptable carrier or diluent.

7. A pharmaceutical composition in dosage unit form for the treatment of allergies which comprises an effective amount of 2-methyl-6,7,8-trimethoxy-1-[4,5,6-triethoxy-7-amino-3-phthalidyl]-1,2,3,4-tetrahydro-isoquinoline and a pharmaceutically acceptable carrier or diluent therefor.

8. A pharmaceutical composition of claim 7, wherein said dosage unit is a tablet.

9. A method for retarding an allergic condition in a patient which comprises administering to said patient an effective amount of a compound of claim 4 or 6.

* * * * *